United States Patent [19]

O'Brien et al.

[11] Patent Number: 4,522,787
[45] Date of Patent: Jun. 11, 1985

[54] ASH FUSION SYSTEM

[75] Inventors: Larry S. O'Brien, St. Joseph; Ward S. Kaler, Benton Harbor, both of Mich.

[73] Assignee: Leco Corporation, St. Joseph, Mich.

[21] Appl. No.: 355,171

[22] Filed: Mar. 5, 1982

[51] Int. Cl.³ .......................................... G01N 31/12
[52] U.S. Cl. ...................................... 422/78; 356/386
[58] Field of Search ............... 422/78, 119; 436/157, 436/148; 356/384–387, 4

[56] References Cited

PUBLICATIONS

Standard Instrumentation, Inc., Catalog "Innovative Instrumentation for the Coal Industry", FA57 Ash Fusion System.
Integrated Systems, Inc., catalog and sheets stating "Recent Projects".
Pages 279–284 of the ASTM American National Standard ANSI/ASTM D 1857–1868 (Reapproved 1974)

"Standard Test Method for Fusibility of Coal and Coke Ash".

Primary Examiner—Hiram H. Bernstein
Attorney, Agent, or Firm—Price, Heneveld, Huizenga & Cooper

[57] ABSTRACT

An ash fusion analyzer for determining the ASTM defined fusion temperatures of coal and coke ash includes a furnace chamber with a viewport. A rotatable sample-supporting platform is positioned within the chamber such that samples on the platform are viewable through the viewport. An optical system is aligned with the viewport for directing images of the moving samples onto a solid state line scan array. A microprocessor is coupled to the array for periodically sampling data from the array and calculating shape information relating to the samples.

28 Claims, 13 Drawing Figures

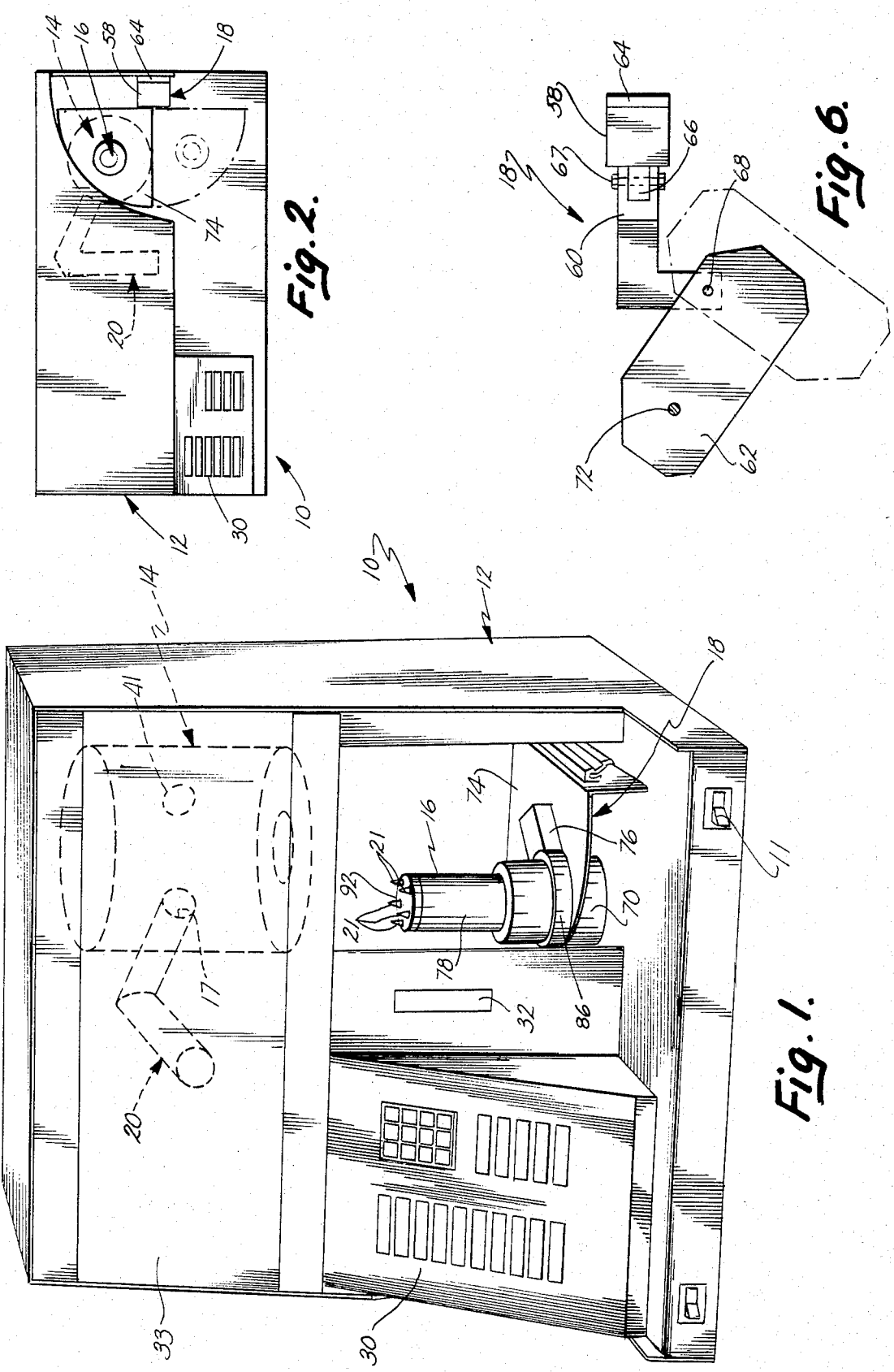

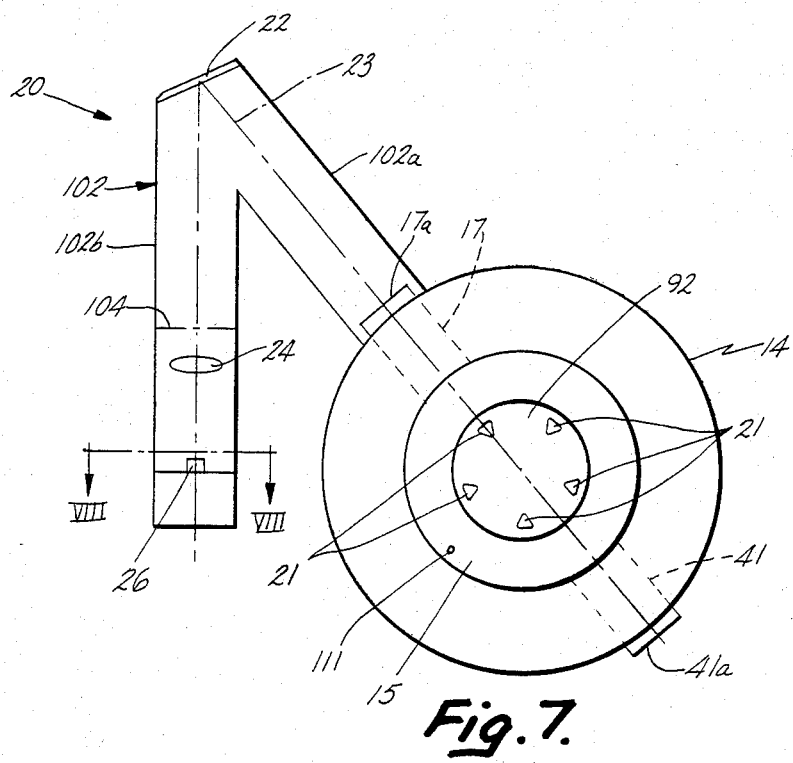
Fig. 7.
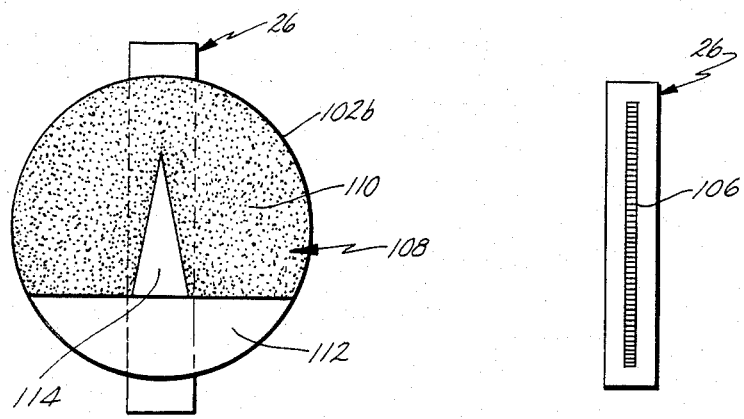
Fig. 8
Fig. 9.

ASH FUSION SYSTEM

BACKGROUND OF THE INVENTION

The present invention relates to analytical devices, and more particularly to analytical devices for determining the fusibility of coal and coke ash.

Before coal or coke is burned in a furnace, the fuel should be analyzed to determine the fusibility of the coal or coke ash. Burning coal or coke in a commercial steel mill furnace, which generates temperatures sufficiently high to fuse the ash, causes the ash to collect on various furnace components, most notably the furnace grates. If collection becomes excessive, the furnace must be shut down, cooled, and cleaned, requiring excessive periods of furnace inactivity.

The ASTM standard test method for determining the fusibility of coal and coke ash requires the ash to be formed into triangular pyramid cones which are placed within an analytical furnace. The temperature within the furnace is then ramped at 15° F. per minute, and the cones are manually observed to detect changes in shape. The fusibility of the ash is reported in four temperatures; namely, (1) the temperature at which the apex of the cone becomes rounded, (2) the temperature at which the height of the deformed cone is equal to the width of the base, (3) the temperature at which the height of the deformed cone is equal to one-half the width of the base, and (4) the temperature at which the cone has been reduced to a lump having a height no greater than one-sixteenth inch. This test method has several significant drawbacks. First, the method is time-consuming and requires an observer to constantly monitor all cones within the furnace as all cones pass through all four stages of fusion. This task is boring and the observer can become inattentive, resulting in inaccurate temperature readings. Second, monitoring the shape of five cones (the typical furnace load) is difficult. Third, the empirical findings are somewhat subject to the individual judgment of the human observer, further introducing error and variation into the test rsults. The ASTM test method recognizes these problems and provides for relatively large acceptable error for each of the four stages of fusion in excess of 50° C. or 100° F.

Although at least two known devices have been developed in an attempt to reduce the time-consuming and tedious chore of observing the cones, these devices are not without their drawbacks. One such device is sold as an add-on unit for conventional furnaces and comprises a closed circuit camera and monitor and a video tape recorder coupled thereto. The operator initiates the test and activates the video tape recorder to make a record of the analysis run. After the test is complete, the operator may replay the tape at a relatively rapid speed to determine the fusibility criteria for each cone. However, this equipment and method is still subject to the individual judgment of the operator in evaluating cone shape. Further, reviewing the entire video tape after a test run is just as tedious and boring as watching the test itself.

Another known device is also sold as an add-on unit for conventional furnaces and includes a closed circuit camera and a computer coupled thereto to analyze the video image on the camera. However, as well as in the above-described unit, the vidicon tubes provide poor performance under the high light intensity of the white-hot cones and furnace interior. Second, the vidicon tubes frequently burn out due in part to the high light intensities involved. Third, the computer required to analyze the video image, and the software implementing the analyzing procedure, is relatively complicated since the computer must distinguish and separately analyze each of the individual cones (typically five) within the furnace which are present in the single video image.

SUMMARY OF THE INVENTION

The aforementioned problems are solved by the present invention. Essentially, an ash fusion system is provided which includes a furnace having a furnace chamber and a sample-supporting platform positioned within the chamber. The analyzer further includes a line scan means and means for synchronously scanning the individual images of the cone samples across the line scan array. In a preferred embodiment, computer circuit means is coupled to the line scan means to sample the data therefrom as the cone images are scanned thereacross and for calculating cone shape information based on the line scan samplings.

In a preferred embodiment of the invention, the line scan means comprises an array of solid-state devices including a plurality of light-sensitive diodes arranged in a linear configuration. Additionally, in the preferred embodiment, the cone image scanning means includes means for rotating the pedestal to provide image movement.

Because the cone images are individually scanned across the line scan array, the computer can simply sample the line scan array as the image passes thereby to quickly determine the current shape of any cone by step-wise integration. This greatly reduces the computer hardware and software required to implement shape analysis. Second, the operator is required only to initiate the system and load and unload samples. This leaves the operator free to operate similar analyzers or other equipment within the laboratory. Third, the tedium of visually continuously observing the cones is eliminated. Fourth, variations produced by the individual judgment of the operator in determining stages of fusibility are also eliminated, being implemented by solid-state devices and computer analysis.

In the preferred embodiment of the invention, the solid-state imaging device has a far longer life under the intense illumination involved than video cameras previously used. This not only improves the reliability of the system, but reduces the need for maintenance and repair.

These and other objects, advantages, and features of the invention will be more fully understood and appreciated by reference to the written specification and appended drawings.

BRIEF DESCRIPTION OF THE DRAWINGS

FIG. 1 is a perspective view of the ash fusion analyzer of the present invention;

FIG. 2 is a top plan view, partially broken away, of the analyzer;

FIG. 6 is a top plan view of the structure shown in FIG. 5;

FIG. 7 is a top plan view of the furnace and optical assembly;

FIG. 8 is a cross-sectional view taken along plane VIII—VIII in FIG. 7 and the inverted image focused on the line scan array;

FIG. 9 is a front elevational view showing the line scan array;

DESCRIPTION OF THE PREFERRED EMBODIMENT

Figure 3:
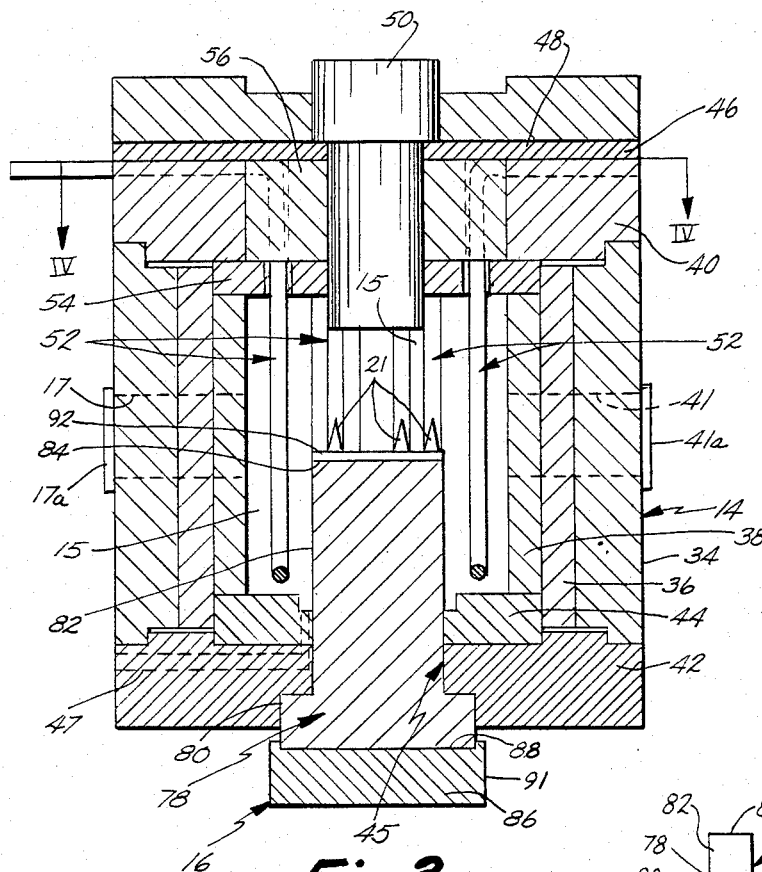
FIG. 3 is a vertical, cross-sectional view of the furnace and sample pedestal.

An ash fusion analyzer constructed in accordance with a preferred embodiment of the invention is illustrated in the drawings and generally designated 10. As seen in FIG. 1, analyzer 10 generally includes housing 12 and a furnace 14 supported within the housing. The furnace has a furnace chamber 15 (FIG. 3) with a viewport 17. A sample pedestal 16, sample transportation mechanism 18 supporting pedestal 16, and an optical assembly 20 are also supported within the housing with assembly 20 aligned with the viewport. Mechanism 18 transports pedestal 16 between an analyze position (see FIG. 3) wherein a sample tray 92, in pedestal 16, is positioned within furnace chamber 15, and a load position (see FIG. 1) wherein the pedestal is positioned for loading and unloading. When in the analyze position, pedestal 16 is rotated to convey the cones 21 supported thereon past viewport 17. Optical assembly 20, as seen in FIG. 7, includes a mirror 22 and lens 24 which directs and focuses the images of cones 21 within chamber 15 onto a line scan array 26. A computer 28 (FIG. 13) is coupled to line scan array 26 and repeatedly samples the line scan array as the cone images are scanned thereacross to calculate information regarding the present shape of the cones. This coneshape information is then analyzed to calculate ash fusibility.

Turning more specifically to the construction of analyzer 10 (FIG. 1), it should be noted that housing 12, furnace 14, pedestal 16, and pedestal transportation mechanism 18 are more fully described in copending application Ser. No. 355,213, entitled ANALYTICAL FURNACE, filed Mar. 5, 1982, by O'Brien et al, assigned to the now U.S. Pat. No. 4,462,963 assignee of the present invention, the disclosure of which is hereby incorporated by reference. Housing 12 includes a keyboard 30 coupled to computer 28 (FIG. 13) for inputting control command information. Additionally, housing 12 supports a display 32 panel with a display also coupled to computer 28 to indicate information regarding the temperature within furnace 14 and the shape of the cones therein.

Furnace 14 (FIG. 3) is generally cylindrical and supported within housing 12. The side wall of furnace 14 includes outer liner 34, middle liner 36, inner liner 38, and a heating element support 40. Liners 34, 36, and 38 are cylindrical and include diametrically opposed viewports, or cylindrical bores, 17 and 41, extending radially therethrough. The bores are covered by single crystal alumina or quartz windows 17a and 41a, respectively. Viewport 41 is visible through a smoked-glass front panel 33, (FIG. 1) while viewport 17 is generally aligned with optical detector 20. The furnace includes a floor 42 and hearth 44 supported thereon. Floor 42 and hearth 44 together define a stepped bore, or aperture, 45 which receives pedestal 16. A gas bore 47 is formed in floor 42 and hearth 44 through which gases can be introduced into chamber 15. A gasket 46, cover 48, and top plug 50 comprise the upper portion of furnace 14. All of the furnace components thus far described, are dimensioned to closely interfit with one another, as described in the referenced application, to provide a relatively tightly closed chamber 15, having a volume of approximately three liters. A plurality of generally U-shaped heating elements 52 extend between element support 40 and gasket 46 and downwardly into furnace chamber 15 so as to be oriented generally parallel to the furnace side wall. Elements 52 are driven by a power source 116 (FIG. 13) coupled to computer 28 by suitable interface circuits included as part of circuit block 28 of FIG. 13. A ceiling member 54 and spacer 56 (see also FIG. 4) cooperate to seal elements 52 within furnace 14.

Transportation mechanism 18 (FIGS. 5 and 6) includes a rodless cylinder 58 actuated by an up/down switch 11 in a conventional manner, a supporting bracket 60, and a support 62, pivotally mounted on the bracket by a pin 68. Cylinder 58 is secured within housing 12 (see FIG. 2) by securing brackets 64, which extend from the cylinder, to the housing. Vertically shiftable element 66 extends from cylinder 58 to travel upwardly and downwardly thereon. Bracket 60 is secured to element 66 by bolts 67. Accordingly, support 62 can pivot in a horizontal plane about pivot pin 68 and can be vertically shifted by actuating cylinder 58 to raise or lower element 66 and bracket 60 supported thereon.

A motor 70 is supported on the underside of support 62 and drives a shaft 72 at approximately ten r.p.m. Worktable 74 is supported in overlying relationship on support 62 and in turn supports sample pedestal 16 and a sensor 76. The sensor is a conventional optical sensor capable of directing light toward an object and sensing the reflectivity of the object against which the light is directed. Sensor 76 is coupled to computer 28 (FIG. 13) to provide rotational positional information regarding pedestal 16.

Figure 10:
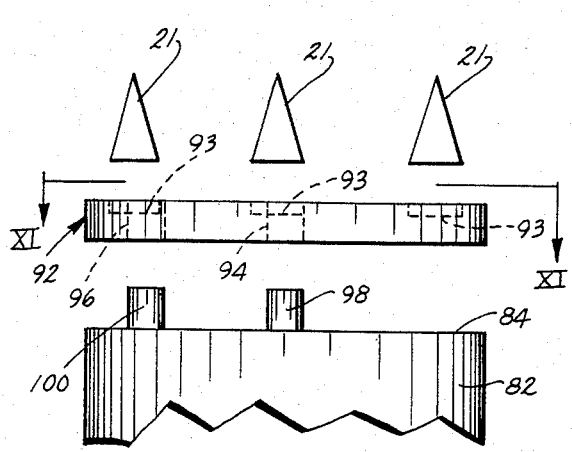
FIG. 10 is a fragmentary, exploded, side elevational view of the sample tray and sample pedestal.
Figure 11:
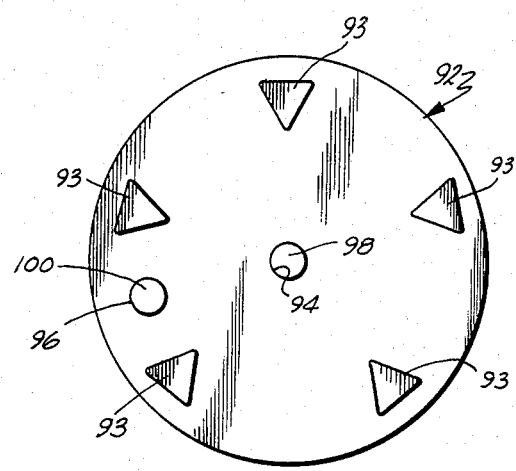
FIG. 11 is a top plan view taken along plane XI—XI in FIG. 10.

Pedestal 16 includes a stepped refractory portion 78 which in turn includes lower cylindrical portion 80 and upper cylindrical portion 82 having a diameter somewhat smaller than the lower portion to generally conform to bore 45. Generally planar sample platform 84 is defined by the upper end of upper portion 82. Pegs 98 and 100 (FIGS. 10 and 11) extend upwardly from platform 84, with peg 98 located at the center of the platform, and peg 100 offset for indexing sample tray 92 thereon.

Figure 5:
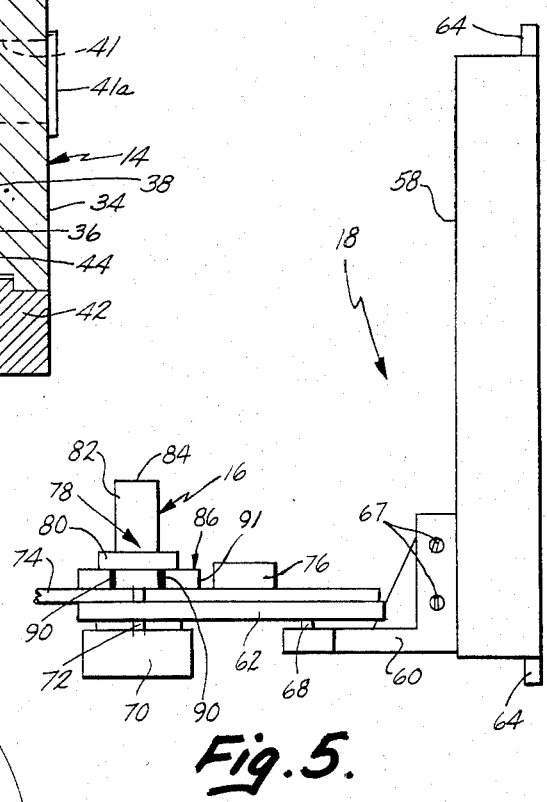
FIG. 5 is a side elevational view of the pedestal transportation mechanism.

The lower portion 80 of refractory element 78 is fixedly supported within an aluminum cup 86 which, as seen in FIG. 5, is fixedly mounted on drive shaft 72 for rotation therewith. Consequently, motor 70 rotates sample platform 84 through shaft 72, cup 86, and refractory element 78. Cup 86 includes a plurality of narrow, vertically extending, light-reflective strips 90 extending around its perimeter surface 92. In the preferred embodiment, perimeter surface 91 is painted black, and reflective strips 90 are formed by cutting away the black enamel at strips 90 to expose the reflective aluminum. One strip 90 is included for each cone sample 21 to be supported on platform 84 and in the preferred embodiment, five such strips are employed. Consequently, as pedestal 16 rotates, sensor 76 can detect reflective strips 90 as the strips pass by the sensor which generates signals responsive to the reflective strips and which indicate information as to alignment of the samples with respect to port 17.

Sample tray 92 (FIGS. 10 and 11) is a generally disc-shaped element having an outer diameter identical to the outer diameter of upper portion 82 of pedestal 16. Tray 92 defines a plurality of circular depressions 93 each of which is approximately one-quarter inch in diameter and approximately one-thirty-second of an inch deep. Depressions 93 receive cone samples 21 sized in accordance with the ASTM standards. Aperture 94 extends through the center of tray 92, and aperture 96 is located radially outwardly therefrom to mate with posts 98 and 100, respectively, on platform 84. Consequently, tray 92 may be placed on platform 84 in only one angular orientation to insure the proper alignment of sample holding depressions 93 with indicator strips 90 on aluminum cup 86.

Figure 4:
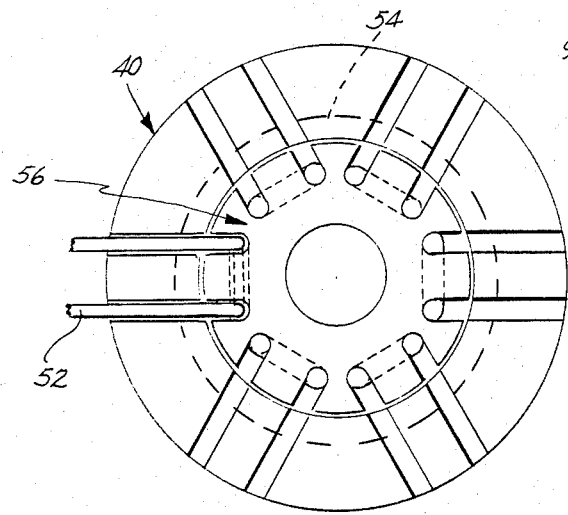
FIG. 4 is a view taken along plane IV—IV in FIG. 3.

Optical assembly 20, most clearly shown in FIG. 7, includes a support tube 102 for supporting a mirror 22, an iris 104, lens 24, and line scan array 26. Support tube 102 is mounted to housing 12 and aligned with viewport 17 which is in turn aligned with sample tray 92 (FIG. 3). Mirror 22 is supported at the junction of tube portions 102a and 102b to project an image from viewport 17 through iris 104 and lens 24 along optical pathway 23. This folded construction greatly improves the compactness of assembly 20. Both iris 104 and lens 24 are generally well known. Iris 104 is a fixed-aperture iris to control the intensity of the image focused on the line scan array. A variable-aperture iris may also be used. Lens 24 is selected to focus the image from viewport 17 onto line scan array 26 such that cones 21, having a height of three-quarters inch are reduced to an image 114 (FIG. 8) one-eighth inch high.

Line scan array 26 (FIGS. 7, 8, and 9) is, in the preferred embodiment, a solid-state, charge-coupled imaging device which is commercially available. As seen in FIG. 9, array 26 includes a generally linear and vertical alignment with a total height of one-quarter inch of light-sensitive diodes 106. In the preferred embodiment, 256 such diodes are employed in an integrated circuit chip, Model No. RL-256G manufactured by EG & G Reticon. Array 26 is positioned within tube portion 102b so that image 108 of viewport 17 is focused on the line scan array (FIG. 8). Image 108 is in turn comprised of background image 110, platform image 112, and cone image 114. Because viewport 41 is relatively cool with respect to platform 92 and cones 21, background image 110 will appear to array 26 to be dark, or black, compared to platform and cone images 112 and 114. Platform 92 and cones 21 which are white-hot produce images 112 and 114 which appear light, or white, compared to background image 110. Consequently, the outline of cone 21 in image 108 is clearly defined. As pedestal 16 rotates, samples are conveyed through the portion of furnace 14 aligned with viewport 17 so that cone images 114 are scanned across line scan array 26. Further, because pedestal 16 continually rotates, the cone images are repeatedly scanned across the array.

A thermocouple 111 (FIGS. 7 and 13) is positioned within chamber 15 and coupled to computer 28. Thermocouple 111 senses the temperature within furnace 14 and generates signals responsive thereto which are received by computer 28 and used as part of a closed loop temperature control for the furnace.

Figure 13:
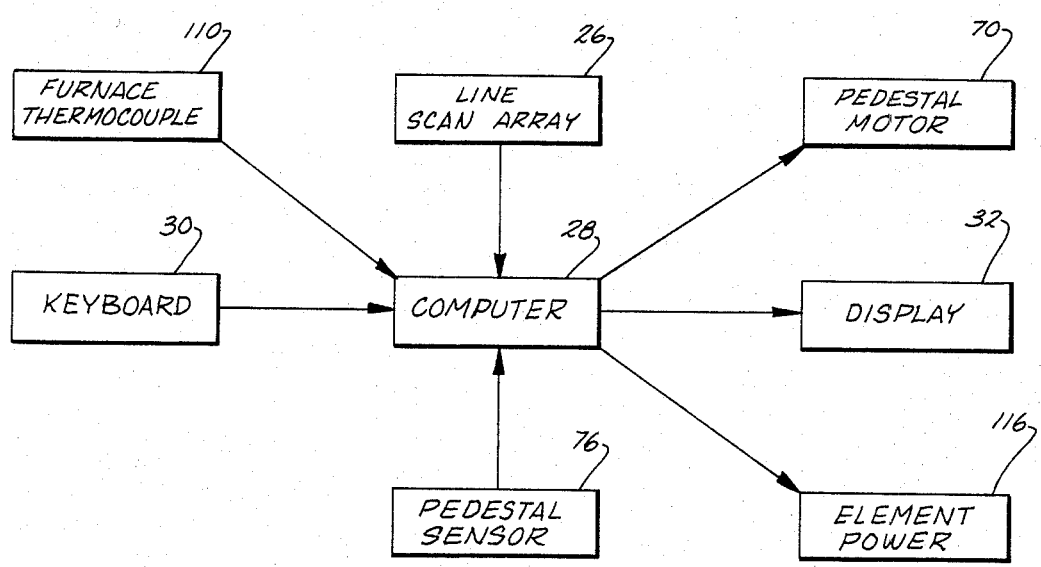
FIG. 13 is an electrical circuit diagram in block form showing the control system for the analyzer.

FIG. 13 shows the overall computer control for analyzer 10. Computer 28 is coupled to line scan array 26, keyboard 30, pedestal sensor 76, and furnace thermocouple 111 by suitable interface circuits to receive signals therefrom. Additionally, computer 28 is coupled to display 32, pedestal motor 70, and element power source 116 by suitable control circuits to provide controlling signals thereto. Display 32 may show cone number, present fusibility stage, and the temperature at which the present fusibility stage was entered. Additionally, computer 28 may be connected to a printer (not shown) to provide a hard copy of information presented on display 32.

Operation

Figure 12:
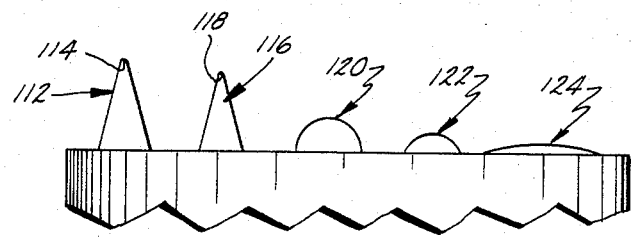
FIG. 12 is a side elevational view illustrating the stages of fusion for a cone sample.

The various fusibility stages to be evaluated by analyzer 10 are illustrated in FIG. 12. The ASTM cone 112 is a pyramid having a triangular base one-quarter of an inch on each side of the base and three-quarters of an inch high. Cone 116 illustrates the cone in its initial deformation temperature wherein apex 118 is just rounded. Cone 120 is in the second stage, designated the softening temperature, wherein the cone has fused down to a spherical lump having a height equal to the width of the base. Cone 122 is at the hemispherical temperature wherein the height of the hemispherical lump is equal to one-half the width of the base. Finally, at the fluid temperature, cone 124 is a fused mass having a maximum height of one-sixteenth inch. The ASTM standard requires all of these temperatures to be determined for each sample.

When an analysis is to be conducted, five separate cones can be analyzed simultaneously with each being formed in accordance with standard ASTM procedures. The five cones 21 are then positioned upright within depressions 93 on plate 92 with each cone seated within one of the depressions. Pedestal 16 is then moved to its loading position as illustrated in FIG. 1, and sample tray 92 is positioned on platform 84 of pedestal 16 by aligning apertures 94 and 96 with studs 98 and 100, respectively, and placing the tray on the platform. Pedestal 16 is then moved to its analyze position within furnace 14 (FIG. 3) so that sample tray 92 and cones 21 are vertically aligned with viewports 17 and 41. The operator then enters a suitable command on keyboard 30 indicating to computer 28 that an analysis is to begin. Computer 28 is conventionally programmed to develope appropriate control signals to element power circuit 116 to actuate elements 52 to elevate the temperature within chamber 15 to the initial temperature of 1500° F., in the preferred embodiment. When the initial temperature has been reached as sensed by thermocouple 111, computer 28 generates a control signal to actuate pedestal motor 70 to rotate at 10 r.p.m. and to power source 116 to ramp the temperature within chamber 15 at 15° F. per minute. Additionally, ASTM-specified gases are introduced into chamber 15 through gas bore 42 in a conventional manner.

As pedestal 16 and sample tray 92 thereon are rotated, the cones are carried through the portion of furnace 14 aligned with viewport 17. The image of chamber 15 obtained through viewport 17 is reflected on mirror 22 and directed through iris 104 and lens 24 onto line scan array 26. Consequently, the images of the cones are repeatedly (at about 580 scans/second) and individually vertically scanned across line scan array 26 as pedestal 16 rotates. During analysis, computer 28 repeatedly samples array 26 by reading each of diodes 106 at a rate of 500 kHz from bottom to top until a light-to-dark transition is detected. Between cones, the sampling of line scan array 26 will establish the top of tray 92. Reflective strips 90 are positioned on aluminum cup 86 so that sensor 76 will detect one of the reflective strips immediately prior to the entry of a cone into viewport 17. Each of reflective strips 90 is unique, so that sensor 76 will issue different signals to computer 28 unique to each one of cones 21. Consequently, computer 28 is capable of determining which of cones 21 is about to be scanned across line scan array 26. In the preferred embodiment, the entire array 26 is sampled approximately every 1.7 milliseconds to provide the desired resolution in determining the shape of cone image 114. The computer then analyzes the stored multiple scan information obtained upon one passage of an image 114 to evaluate the shape of the cone.

Computer 28 is programmed in a conventional manner to compare the temporarily stored scan information with stored data corresponding to the four fusibility stages by the following criteria. A cone is determined to have obtained its initial deformation temperature when the peak of the cone has shrunk one-sixteenth, or sixty thousandths of an inch. The cone has attained its softening and hemispherical temperatures when the height is equal to the width of the base and one-half of the width of the base, respectively. Finally, the fluid temperature is attained when the height of the cone is no greater than one-sixteenth or sixty thousandths of an inch. As computer 28 determines that one of the fusibility stages has been attained, it stores this information including cone number, fusibility stage, and the temperature as sensed by thermocouple 111 at which the stage was entered into. This information is displayed on display 32 and in the preferred embodiment is printed on a printer at the conclusion of the analysis to provide a hard copy of the analysis results. Because the temperature is ramped at 15° F. per minute, and because pedestal 16 rotates at 10 r.p.m., the accuracy of each fusibility stage temperature is determined with an accuracy of ±1.5° F. This accuracy is a vast improvement over the acceptable ASTM accuracy of ±50° F.

When the temperature within chamber 15 has risen above the fluid temperatures of all of the cones on tray 92, computer 28 issues a control signal to element power source 116 to deactivate elements 52 and to deactivate pedestal motor 70. When the operator activates the cylinder up/down switch 11, the pedestal may be moved to its unloading position as shown in FIG. 1 whereupon the sample tray 92 is removed from pedestal 16 and discarded. Analyzer 10 is then ready for the next analysis run.

It should be understood that the above description is intended to be that of a preferred embodiment of the invention. Various changes and alterations might be made without departing from the spirit and broader aspects of the invention as set forth in the appended claims, which are to be interpreted in accordance with the principles of patent law, including the doctrine of equivalents.

The embodiments of an invention in which an exclusive property or privilege is claimed are defined as follows:

1. An analyzer furnace comprising:
a furnace defining a chamber;
radiation responsive detection means for detecting radiation along a line oriented in a first direction and producing signals responsive to an image focused thereon;
means for projecting the image of a portion of said furnace chamber onto said detection means;
means for supporting a plurality of samples within said furnace chamber and for repeatedly conveying said samples individually through said chamber portion in such manner to cause the individual images of said samples to be repeatedy projected across said detection means in a second direction generally perpendicular to said first direction; and
circuit means coupled to and responsive to said detection means for determining shape information of each sample.

2. The apparatus as defined in claim 1 wherein said sample supporting means comprises a sample support device and means for rotating said device to move a sample within said chamber in a predetermined path of movement.

3. The apparatus as defined in claim 2 wherein said device includes means for indicating the angular orientation of each of said samples within said chamber.

4. The apparatus as defined in claim 1 wherein said projection means comprises a viewport extending through said furnace in alignment with said sample support device and optical means for focusing radiation from said viewport onto said detection means.

5. The apparatus as defined in claim 4 wherein said detection means comprises a solid-state imaging device formed of a linear array of detection elements.

6. The apparatus as defined in claim 5 wherein said radiation falls within the visible spectrum and said array is a plurality of light-sensitive diodes.

7. The apparatus as defined in claim 1 wherein said circuit means includes a computer for comparing information from said detection means with stored information and for providing output signals representing the existance of a comparison.

8. An ash fusion analyzer comprising:
a furnace including a chamber for the fusion of a plurality of samples therein;
detection means positioned remote from said chamber for detecting radiation along a line and producing signals responsive to an image projected thereon;
means for projecting the image of a portion of said furnace chamber onto said detection means;
means for supporting one or more samples within said furnace chamber and for repeatedly conveying said samples sequentially through said chamber portion so that the image of said samples are individually repeatedly projected across said detection means in a direction generally perpendicular to said line; and
circuit means coupled to and responsive to signals from said detection means for calculating shape information relating to the shape of said samples.

9. An ash fusion analyzer as defined in claim 8 wherein said sample supporting means comprises:
a sample-supporting device; and
means for rotating said device.

10. An ash fusion analyzer as defined in claim 9 wherein said sample-supporting device includes means for locating each sample thereon and for indicating the angular orientation of each of said samples within said chamber.

11. An ash fusion analyzer as defined in claim 10 wherein said analyzer further comprises sensor means coupled to said circuit means for producing signals responsive to said indicating means, whereby said circuit means determines which of said samples is in said chamber portion.

12. An ash fusion analyzer as defined in claim 11 wherein said projection means includes a viewport formed through a wall of said furnace and enclosed by a window, said viewport aligned with said chamber portion.

13. An ash fusion analyzer as defined in claim 8 wherein said detection means comprises a solid-state imaging device.

14. An ash fusion analyzer as defined in claim 13 wherein said solid-state imaging device comprises a generally linear array of light-sensitive diodes.

15. An ash fusion analyzer as defined in claim 14 wherein said solid-state imaging device comprises a charge-coupled integrated circuit.

16. An ash fusion analyzer as defined in claim 8 wherein said detection means comprises a line scan array of detectors.

17. An ash fusion analyzer as defined in claim 16 wherein said array comprises a plurality of light-sensitive diodes.

18. An ash fusion analyzer as defined in claim 8 further comprising means coupled to said circuit means for sensing the temperature within said chamber and producing signals responsive thereto.

19. An ash fusion analyzer as defined in claim 18 further comprising means coupled to said circuit means for displaying said shape information.

20. An ash fusion analyzer as defined in claim 19 wherein said circuit means comprises a computer programmed means for correlating sample shape information with said furnace chamber temperature.

21. An ash fusion system comprising:
a furnace having a temperature-controllable chamber;
platform means for supporting a plurality of samples within said chamber;
line scan means for sampling light intensity along a line and producing signals responsive thereto;
means for projecting repetitive images of each sample across said line scan means in a direction generally perpendicular to said line;
computer means coupled to said line scan means for sampling said signals as said images are projected across said line scan means and for calculating sample shape information; and
display means for displaying said shape information.

22. An ash fusion system as defined in claim 21 wherein said line scan means comprises a linear array of light-sensitive diodes.

23. An ash fusion system as defined in claim 21 wherein said projection means includes means for rotating said platform means.

24. An ash fusion system as defined in claim 23 wherein said platform means further comprises means for indicating the angular orientation of each sample on said rotating platform means; and wherein said system further comprises means coupled to said computer means for generating signals responsive to said indicating means.

25. An ash fusion system as defined in claim 21 wherein each of said samples is assigned a unique identifier; and wherein said display means displays said shape information for said each sample in conjunction with said identifier assigned to said each sample.

26. An ash fusion system as defined in claim 21 further comprising means coupled to said computer means for sensing the temperature within said furnace chamber and generating signals responsive thereto.

27. An ash fusion system as defined in claim 26 wherein said display means displays said shape information in conjunction with the temperature within said furnace chamber.

28. An ash fusion system as defined in claim 21 wherein said furnace includes wall means and said projection means includes a viewport formed through said wall means.

* * * * *

UNITED STATES PATENT AND TRADEMARK OFFICE
CERTIFICATE OF CORRECTION

PATENT NO. : 4,522,787
DATED : June 11, 1985
INVENTOR(S) : O'Brien et al.

It is certified that error appears in the above-identified patent and that said Letters Patent is hereby corrected as shown below:

Column 1, line 41:

"rsults" should be --results--

Column 3, line 49-50 should read:

--FURNACE, filed March 5, 1982, by O'Brien et al, now U.S. Patent 4,462,963 7/31/84, assigned to the assignee of--

Signed and Sealed this

Seventeenth Day of December 1985

[SEAL]

Attest:

DONALD J. QUIGG

Attesting Officer

Commissioner of Patents and Trademarks